United States Patent [19]

Linn et al.

[11] Patent Number: 5,023,241
[45] Date of Patent: Jun. 11, 1991

[54] AVERMECTIN DERIVATIVES

[75] Inventors: Bruce O. Linn, Bridgewater; Helmut Mrozik, Matawan, both of N.J.

[73] Assignee: Merck & Co., Inc., Rahway, N.J.

[21] Appl. No.: 387,207

[22] Filed: Jul. 31, 1989

[51] Int. Cl.$^5$ .................... A61K 31/70; C07H 17/04
[52] U.S. Cl. ........................................ 514/30; 536/7.1
[58] Field of Search ............................ 514/30; 536/7.1

[56] References Cited

U.S. PATENT DOCUMENTS

| | | | |
|---|---|---|---|
| 4,199,569 | 4/1980 | Chabala et al. | 536/7.1 |
| 4,206,205 | 6/1980 | Mrozik et al. | 514/30 |
| 4,310,519 | 1/1982 | Albers-Schonberg et al. | 514/30 |
| 4,427,663 | 1/1984 | Mrozik | 514/30 |
| 4,806,527 | 2/1989 | Christensen et al. | 536/7.1 |
| 4,831,016 | 5/1989 | Mrozik et al. | 536/7.1 |

FOREIGN PATENT DOCUMENTS

| | | |
|---|---|---|
| 214731 | of 0000 | European Pat. Off. |
| 276103 | of 0000 | European Pat. Off. |
| 276131 | of 0000 | European Pat. Off. |
| 301806 | 2/1989 | European Pat. Off. |

OTHER PUBLICATIONS

Chen et al., Abstr. Pap Am. Chem. Soc. (186 Meet, MBTD 28, 1983).
Schulman et al (I), *J. Antibiotic* 38, pp. 1494–1498 (1985).
Schulman et al. (II), *Antimicrobial Agents and Chemotherapy* 31, pp. 744–747 (1987).
Fisher et al., *Macrolide Antibiotics,* Omura (Ed.) Academic Press, New York, pp. 553–606 (1984).
Davies et al., Nat. Prod. Rep. 3, pp. 87–121 (1986).

*Primary Examiner*—Elli Peselev
*Attorney, Agent, or Firm*—David L. Rose; Michael C. Sudol

[57] ABSTRACT

Novel avermectin derivatives are disclosed, wherein the 4"-hydroxy group is replaced by a substituted acylamino or benzoylamino group. These avermectin derivatives can be further derivatized at the 5- and 23-positions as ketoximes or O-substituted ketoximes. The 4"-substituted avermectin derivatives are prepared by the acylation of the known 4"-aminoavermectins with acylating reagents. The new compounds are potent antiparasitic agents, in particular, the compounds are anthelmintic, insecticidal and acaricidal agents.

14 Claims, No Drawings

AVERMECTIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted at the 13 position with a 4-(alpha-L-oleandrosyl)-alpha-L-oleandrose group. The avermectin compounds and the instant derivatives thereof have a very high degree of anthelmintic and anti-parasitic activity.

The avermectin series of compounds isolated from the fermentation broth have the following structure:

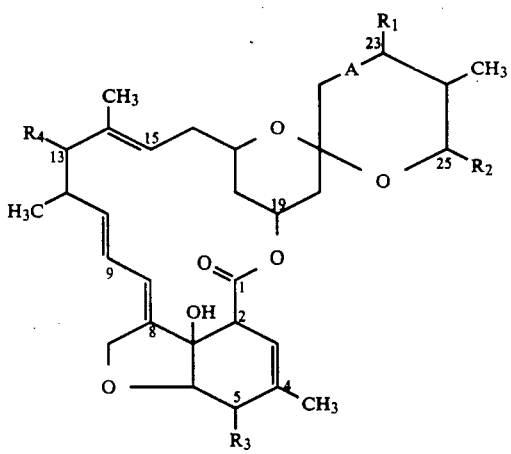

wherein $R_4$ is the 4'-α-(L-oleandrosyl)-α-L-oleandrosyloxygroup of the structure

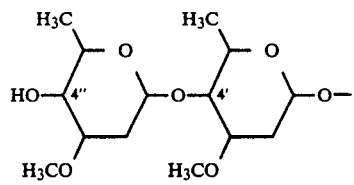

and wherein
A at the 22,23 position indicates a single or a double bond;
$R_1$ is a hydrogen or hydroxy and is present only when A indicates a single bond;
$R_2$ is iso-propyl or sec-butyl; and
$R_3$ is methoxy or hydroxy.

There are eight different avermectin natural product compounds and they are given the designations A1a, A1b, A2a, A2b, B1a, B1b, B2a, and B2b based upon the structure of the individual compounds. In the foregoing structural formula, the individual avermectin compounds are as set forth below. (The R group is 4'-α(L-oleandrosyl)α-L-oleandrosyloxy:

|     | (A)         | $R_1$ | $R_2$     | $R_3$  |
|-----|-------------|-------|-----------|--------|
| A1a | double bond | —     | sec-butyl | —OCH$_3$ |
| A1b | double bond | —     | iso-propyl| —OCH$_3$ |
| A2a | single bond | —OH   | sec-butyl | —OCH$_3$ |

-continued

|     | (A)         | $R_1$ | $R_2$     | $R_3$  |
|-----|-------------|-------|-----------|--------|
| A2b | single bond | —OH   | iso-propyl| —OCH$_3$ |
| B1a | double bond | —     | sec-butyl | —OH    |
| B1b | double bond | —     | iso-propyl| —OH    |
| B2a | single bond | —OH   | sec-butyl | —OH    |
| B2b | single bond | —OH   | iso-propyl| —OH    |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, optionally further substituted by heteroatoms such as oxygen, sulfur, nitrogen, and halogen, are known in the literature. These derivatives are obtained through various adjustments and additions to the fermentation procedures as described fully in the European Patent Application EPO 0 214 731.

Avermectins are products of microbial fermentations using the actinomycete *Streptomyces avermitilis*. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from aminoacids L-valine and L-isoleucine, respectively. It was reasoned, that these aminoacids are deaminated to the corresponding 2-ketoacids, and that these then are decarboxylated to give 2-methylpropionic and 2-methylbutyric acids. These acids then have been found to be directly incorporated into the avermectin structures to give the 2-propyl and 2-butyl C-25 substituents, as is reported by Chen et al., Abstr. Pap. Am. Chem. Soc. (186 Meet.,MBTD 28, 1983). It was also disclosed in European Patent Application number 0 214 731 that additions of large amounts of other acids such as cyclopentanoic, cyclobutyric, 2-methylpentanoic, 2-methylhexanoic, thiophene-3-carboxylic acids and others to the fermentation broth of S. avermitilis causes the microbes to accept these acids as substitutes and to make small amounts of avermectins containing these acids in form of new C-25 substituents. Examples of such new avermectin derivatives are: 25-(thien-3-yl)-25-de-(1-methylpropyl)avermectin A2a 25-(cyclohex-3-enyl)-25-de-(1-methylpropyl)avermectin A2a 25-cyclohexyl-25-de-(1-methylpropyl)avermectin A2a 25-(1-methylthioethyl)-25-de-(1-methylpropyl) avermectin A2a 25-(2-methylcyclopropyl)-25-de-(1-methylpropyl) avermectin A2a Similar experiments producing avermectins "c" and "d" containing as C-25 substituents a 2-pentyl and 2-hexyl group are described by T. S. Chen et al. in Arch. Biochem. Biophys. 1989, 269, 544–547.

Still additional avermectin derivatives are produced through artificial modification of the fermentation of *Streptomyces avermitilis* either by addition of metabolic inhibitors such as sinefungin (as described by Schulman et al., J. Antibiot. 1985, 38, 1494–1498) or by mutation of the parent strain (as described by Schulman et al., Antimicrobial Agents and Chemotherapy, 1987, 31, 744–747, and by EP-276-131-A to Pfizer INC.). Some of these avermectin derivatives are still further modified and are missing one or two of the 3'- and 3"-O-methyl groups (Schulman et al., *J. Antibiot.* 1985, 38, 1494–1498). Examples for such derivatives are:

3',3"-Bisdesmethylavermectin B1a and B1b
3',3"-Bisdesmethylavermectin B2a and B2b
3"-Desmethylavermectin B1a and B1b
3"-Desmethylavermectin B2a and B2b
3',3"-Bisdesmethyl-25-cyclohexyl-25-de-(2-butyl)avermectin B2a
3',3"-Bisdesmethyl-25-cyclopentyl-25-de-(2-butyl)avermectin B2a
3',3"-Bisdesmethyl-25-(3-thienyl)-25-de-(2-butyl)avermectin B2a
3',3"-Bisdesmethyl-25-(3furyl)-25-de-(2-butyl)avermectin B2a
3',3"-Bisdesmethyl-25-(1-methylthioethyl)-25-de-(2-butyl)avermectin B1a.

The fermentation products have been chemically modified in order to obtain further antiparasitic and insecticidal analogs with improved properties. Publications of such procedures in the scientific and patent literature have been reviewed by Fisher, M. H.; Mrozik, H. In Macrolide Antibiotics; Omura, S., Ed.; Academic: New York, 1984; pp 553–606, and by Davies, H. G.; Green, R. H. Nat. Prod. Rep., 1986, 3, 87–121.

For example a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties. Other examples of semisynthetic avermectin derivatives contain a 8,9-oxide group, a 4a-hydroxy or acyloxy group, a 23-keto group, which all are potent antiparasitic and insecticidal compounds.

It has also been described by Mrozik in U.S. Pat. No. 4,427,663 that amino substituents at the 4"- and 4'- positions have very high antiparasitic and insecticidal activities.

These compounds may be used as starting materials for the compounds of the instant invention without further modification, or when containing additional reactive groups, which are not to be modified under the reaction conditions applied, only after protection of such with a suitable protecting group.

SUMMARY OF THE INVENTION

The instant invention is concerned with derivatives of avermectin compounds wherein the 4"-hydroxy group is replaced by a substituted acylamino group. The substituted acylamino analogs may also be further modified. Thus it is the object of this invention to describe such compounds. It is a further object of this invention to describe the processes useful for the preparation of such compounds. A still further object is to describe the use of such compounds as anthelmintic, insecticidal, and acaricidal agents. Still further objects will become apparent from the reading of the following description.

DESCRIPTION OF THE INVENTION

The compounds of the instant invention have the following structural formula:

wherein
A at the 22,23 position represents a single bond and wherein $R_1$ is hydrogen or hydroxy or oxo, or A represents a double bond and $R_1$ is absent;

$R_2$ is methyl, ethyl, an alpha-branched $C_3$-$C_8$ alkyl, alkenyl, alkynyl, alkoxyalkyl or alkylthioalkyl group; a $C_3$-$C_8$ cycloalkyl or $C_5$-$C_8$ cycloalkenyl group, either of which may optionally be substituted by methylene or one or more $C_1$-$C_4$ alkyl groups or halo atoms; or a 3 to 6 membered oxygen or sulfur containing heterocyclic ring which may be saturated, or fully or partly unsaturated and which may optionally be substituted by one or more $C_1$-$C_4$ alkyl groups or halo atoms;

$R_3$ is hydroxy, loweralkoxy, loweralkanoyloxy, oxo or oxime;

$R_4$ is or where $R_5$ is $NR_6R_7$, $R_6$ is substituted loweralkanoyl, where the substituent is halogen, hydroxy, loweralkoxy, phenoxy, loweralkylthio, loweralkylsulfinyl, loweralkylsulfonyl, amino, loweralkanoylamino, loweralkylamino, haloloweralkoxycarbonylamino, oxo, carboxy or loweralkoxycarbonyl; or $R_6$ is cycloloweralkanoyl, or benzoyl, or substituted benzoyl, wherein the substituent is halogen, loweralkoxy, sulfonamido, amino, loweralkylamino, diloweralkylamino or loweralkanoylamino; or $R_6$ is nicotinoyl;

$R_7$ is hydrogen, loweralkyl, substituted loweralkyl where the substituent is phenyl, hydroxy, loweralkoxy, amino, loweralkylamino, loweralkanoylamino, methylthio, methylsulfonyl or methylsulfinyl;
or $R_5 =$

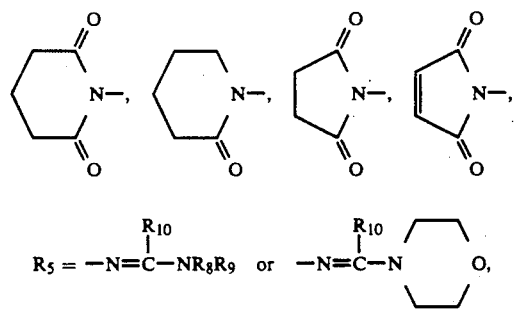

$R_5 = -NH-CO-NR_8R_9$,
$R_8$, $R_9$ and $R_{10}$ are independently hydrogen or loweralkyl;
or $R_5 = -NH-CN$.

Preferred compounds of the instant invention are realized in the foregoing structural formula wherein A at the 22,23 position represents a single bond and wherein $R_1$ is hydrogen or hydroxy, or A represents a double bond and $R_1$ is absent;
$R_2$ iso-propyl, sec-butyl, or an alpha-branched $C_3$-$C_8$ alkenyl group; and
$R_3$ is hydroxy or oxime;
$R_4$ is

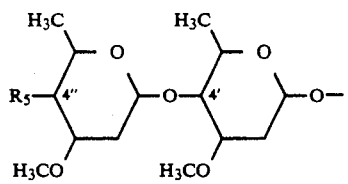

where $R_5$ is $NR_6R_7$,
$R_6$ is substituted loweralkanoyl, where the substituent is halogen, hydroxy, loweralkoxy, phenoxy, loweralkylthio, loweralkylsulfinyl, loweralkylsulfonyl, amino, loweralkanoylamino, loweralkylamino, haloloweralkoxycarbonylamino, oxo, carboxy or alkoxycarbonyl; or $R_6$ is cycloloweralkanoyl, or benzoyl, or substituted benzoyl, wherein the substituent is halogen, loweralkoxy, sulfonamido, amino, loweralkylamino, diloweralkylamino or loweralkanoyl; or $R_6$ is nicotinoyl;
$R_7$ is hydrogen, loweralkyl, substituted loweralkyl where the substituent is phenyl, hydroxy, loweralkoxy, amino, loweralkanoylamino, loweralkanoyl, methylthio, methylsulfonyl or methylsulfinyl;
or $R_5 = -NH-CO-NR_8R_9$,
where $R_8$ and $R_9$ and $R_{10}$ are independently hydrogen or loweralkyl.

The most preferred compounds are realized in the foregoing structural formula wherein A at the 22,23 position represents a single bond and wherein
$R_1$ is hydrogen or hydroxy, or A represents a double bond and $R_1$ is absent;
$R_2$ is 2-propyl, 2-butyl, 2-buten-2-yl, 2-penten-2-yl, or 4-methyl-2-penten-2-yl;
$R_3$ is hydroxy;
$R_4$ is

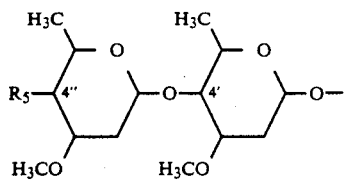

where $R_5$ is $NR_6R_7$,
$R_6$ is substituted loweralkanoyl, where the substituent is halogen, hydroxy, loweralkoxy, phenoxy, loweralkylthio, loweralkylsulfinyl, loweralkylsulfonyl, amino, loweralkanoyl, loweralkylamino, haloloweralkoxycarbonylamino, oxo, carboxy or loweralkoxycarbonyl; or $R_6$ is lowercycloalkanoyl, or benzoyl, or substituted benzoyl, wherein the substituent is halogen, loweralkoxy, sulfonamido, amino, loweralkylamino, diloweralkylamino or loweralkanoyl; or $R_6$ is nicotinoyl;
$R_7$ is hydrogen, loweralkyl, substituted loweralkyl where the substituent is phenyl;
or $R_5 = -NH-CO-NR_8R_9$,
where $R_8$ and $R_9$ and $R_{10}$ are independently hydrogen or loweralkyl.

Preferred compounds of the instant invention are further realized in the following compounds:
4''-deoxy-4''-epi-methoxyacetylaminoavermectin B1a/B1b
4''-deoxy-4''-methoxyacetylaminoavermectin B1a/B1b
4''-deoxy-22,23-dihydro-4''-epi-methoxyacetylaminoavermectin B1a/B1b
4''-deoxy-4''-epi-methoxyacetylaminoavermectin B2a/B2b
25-cylopentyl-25-de-(1-methylpropyl)-4''-epi-methoxyacetylaminoavermectin B1a
4''-deoxy-4''-epi-(N-methoxyacetyl-N-methylamino)avermectin B1a/B1b
4''-deoxy-4''-epi-methylthioacetylaminoavermectin B1a/B1b
4''-deoxy-4''-epi-methylsulfinylacetylaminoavermectin B1a/B1b
4''-deoxy-4''-epi-methylsulfonylacetylaminoavermectin B1a/B1b
4'-deoxy-4'-epi-methylthioacetylaminoavermectin B1a/B1b monosaccharide
4''-deoxy-4''-epi-glycylaminoavermectin B1a/B1b
4''-epi-(N-acetylglycylamino)-4''-deoxyavermectin B1a/B1b
4''-deoxy-4''-epi-(2-hydroxypropionylamino)avermectin B1a/B1b
4''-deoxy-4''-epi-phenoxyacetylaminoavermectin B1a/B1b
4''-deoxy-4''-epi-(2,2,2-trichloroethoxycarbonyl)-glycylaminoavermectin B1a/B1b
4''-epi-benzoylamino-4''-deoxyavermectin B1a/B1b
4''-epi-(4-chlorobenzoylamino)-4''-deoxyavermectin B1a/B1b
4''-epi-(4-methoxybenzoylamino)-4''-deoxyavermectin B1a/B1b
4''-epi-(3-chloro-4-aminosulfonylbenzoylamino)-4''-deoxyavermectin B1a/B1b
4''-deoxy-4''-epi-nicotinoylamino-4''-avermectin B1a/B1b
4''-epi-cyclohexylcarbonylamino-4''-deoxyavermectin B1a/B1b
4''-epi-(3-chloro-4-dimethylaminobenzoylamino)-4''-deoxy avermectin B1a/B1b 4″-deoxy-4″-epi-(2,2,2-trimethylacetylamino)-avermectin B1a/B1b
4″-epi-chloroacetylamino-4″-deoxyavermectin B1a/B1b
4″-deoxy-4″-epi-(phenylalanylamino)avermectin B1a/B1b
4″-deoxy-4″-epi-(N-methoxycarbonyl-N-methylamino)avermectin B1a/B1b
4″-deoxy-4″-epi-methoxycarbonylaminoavermectin B1a/B1b
4″-deoxy-4″-epi-(2-methylpropyloxy)carbonylaminoavermectin B1a/B1b
4″-deoxy-4″-epi-phenoxycarbonylaminoavermectin B1a/B1b
4″-deoxy-4″-(methylaminocarbonyl)aminoavermectin B1a/B1b
4″-deoxy-4″-(phenylaminocarbonyl)aminoavermectin B1a/B1b
4″-deoxy-4″-(2-propylaminocarbonyl)aminoavermectin B1a/B1b
4″-deoxy-4″-(iminomethyleneamino)avermectin B1a/B1b
4″-deoxy-4″-(dimethylaminomethyleneimino)avermectin B1a/B1b
4″-deoxy-4″-(N-morpholinylmethyleneimino)avermectin B1a/B1b
4″-epi-amino-4″-deoxyavermectin B1a/B1b N,N-dimethylacetamidine In the instant invention the term "loweralkyl" is intended to indicate those alkyl groups of from 1 to 6 carbon atoms such as methyl, ethyl, propyl, isopropyl, butyl, pentyl, hexyl, and the like.

The term "loweralkoxy" is intended to include those alkoxy groups of from 1 to 6 carbon atoms such as methoxy, ethoxy, propoxy, isopropoxy, butoxy, pentoxy, hexoxy, and the like.

The term "loweralkanoyl" is intended to include those alkanoyl groups of from 1 to 6 carbon atoms such as formyl, acetyl, propionyl, butyryl, pentanoyl, hexanoyl, and the like.

The term "cycloloweralkanoyl" is intended to include those cycloalkanoyl groups of from 3 to 6 carbon atoms such as cyclopropionyl, cyclobutyroyl, cyclopentanoyl, cyclohexanoyl and the like.

The term "halogen" is intended to include the halogen atoms, fluorine, chlorine, bromine, or iodine.

The above structural formula is shown without a definitive stereochemistry. However, during the course of the synthetic procedures used to prepare such compounds, the products of such procedures can be a mixture of stereoisomers. In particular, the stereoisomers at the 4″-, 4′-, 13- and 23-positions may be oriented either α- or β- representing such groups being below or above the general plane of the molecule, respectively. In each such case both the α- and β-configurations are intended to be included within the ambit of this invention. In certain cases the term "epi" is used to distinguish the stereoisomer being of opposite configuration to the natural compound at one specific assymmetrical carbon atom.

PREPARATION OF STARTING MATERIALS

The ultimate starting materials for the compounds of this invention are the avermectin fermentation products defined above. In addition, other microbially produced avermectin derivatives containing an alpha branched alkyl or alkenyl group substituent at the 25 position designated in the structural formula as $R_2$ have been described in European patent application number 86305604.0 (publication number 0 214 731), 88300426.9 (0 276 131), and 88300354.3 (0 276 103). These compounds can also be used as starting materials for the compounds claimed in this invention. The $R_2$ substituent is inert under the reaction conditions employed for the preparation of the compounds of this invention, so that these reactions can also be carried out with these altered avermectin derivatives. It is apparent that additional reactions are required to prepare the starting materials for the instant compounds. Specifically, reactions are carried out at the 4″, 4′, 5, 22, and 23-positions. It is generally preferred to prepare whatever substituents are required at the 5, 22, 23 or other positions before the oxidation at the 4″- or 4′-hydroxy group, reductive amination of the thus produced 4″- or 4′-ketone to the 4″- or 4′-aminocompounds and their subsequent acylation. Such a reaction sequence generally avoids undesirable side reactions. This technique is not required, however, and if desired other sequences may be used. In addition, during the oxidation and certain substitution reactions described above, it is necessary to protect the 5-hydroxy group to avoid oxidation or substitution at that position. With this position protected the reactions may be carried out at the 4″- or 4′-positions without affecting the remainder of the molecule. Subsequent to any of the above described reactions the protecting group may be removed and the unprotected product isolated. The protecting group employed is ideally one which may be readily synthesized, will not be affected by the reactions at the 4″-and 4′-positions and may be removed without affecting any other functionality of the molecule. One preferred type of protecting group for the avermectin type of molecule is the tri-substituted silyl group, preferably the trialkyl silyl group. One especially preferred example is the t-butyldimethylsilyl group. The reaction preparing the protected compound is carried out by reacting the hydroxy compound with the appropriately substituted silylhalide, preferably the silylchloride in an aprotic polar solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred amines are imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours. The silyl group is removed by stirring the silylated compound in methanol catalyzed by an acid preferably a sulfonic acid monohydrate such as p-toluenesulfonic acid monohydrate. The reaction is complete in about 1 to 12 hours at from 0° to 50° C. Alternatively, the silyl group may be removed by treatment of the silyl compound with anhydrous pyridine-hydrogen fluoride in tetrahydrofuran. The reaction is complete in from 3 to 24 hours at from 0° to 25° C.

Another of the starting materials used in the foregoing reaction scheme are those in which the 22,23, double bond has been reduced to a single bond. The preferred catalyst for the selective hydrogenation of the 22,23 double bond is one having the formula:

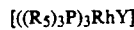

wherein $R_5$ is loweralkyl, phenyl, or loweralkyl substituted phenyl and Y is halogen. The reduction is completely described in U.S. Pat. No. 4,199,569.

The other starting materials which are used in the above reaction scheme involve the preparation of the monosaccharide. The processes which may be used to prepare the monosaccharide derivatives of the avermectin compounds are described in U.S. Pat. No. 4,206,205. The reaction consists generally of treating the starting disaccharide with acid in an aqueous organic solvent mixture. Water concentration of from 0.1 to 20% by volume and acid concentrations of from about 0.01 to 0.1% will predominantly produce the monosaccharide.

A procedure for the preparation of the monosaccharide utilizes a 1% mineral acid solution in isopropanol at 20° to 40° C. for from 6 to 24 hours. Mineral acids such as sulfuric, phosphoric, and the like may be employed.

In all cases the substituent at the 25-position of the avermectin is inert to the reaction conditions and the presence of alkyl groups, alkenyl groups, cycloalkyl groups, cycloalkenyl groups and the like at this position will little affect the preparation, isolation, or activity of the avermectin derivative.

PREPARATION OF COMPOUNDS

The preparation of the instant compounds requires that the avermectin starting materials are oxidized at the 4"or 4'-positions to the corresponding ketones, which are then reductively aminated using NaCNBH$_3$ as reducing agent and ammonium acetate as the source for the amino group. The thus obtained 4"-amino-4"-deoxyavermectin derivatives are used as the substrate for the acylation reaction. The 5-hydroxy groups are protected by a tert-butyldimethylsilyl-group before the oxidation, but the 23-hydroxy group is less reactive and the 7-hydroxy group is very unreactive and these need not be protected. The starting materials containing oxo-, amino-, alkylamino-, or alkanoylamino-substituents at the 4"- or 4'-positions are described by Mrozik in U.S. Pat. No. 4,427,663. For this purpose the 4"- or 4'-hydroxygroups are oxidized in an inert solvent such as methylene chloride using oxalyl chloride or trifluoroacetic anhydride and dimethylsulfoxide as the oxidizing agent. The reaction proceeds by dissolving the oxalyl chloride or trifluoroacetic anhydride and dimethylsulfoxide in methylene chloride with cooling from $-50°$ to $-80°$ C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4"- or 4'-keto compound is isolated using techniques known to those skilled in the art.

Then the 4"- or 4'-ketoavermectin is aminated to prepare the unsubstituted amino compound. The reaction is carried out in an inert solvent such as methanol at from $-25°$ to 10° C. using ammonium salts such as ammonium acetate or ammonium chloride and sodium cyanoborohydride as the aminating and reducing reagents. The reaction is complete in from 15 minutes to 2 hours and the product 4"deoxy-4"-amino compound is isolated by techniques known to those skilled in the art. The reduction of the 4"- or 4'-carbonyl compounds to the corresponding aminoderivatives can give two epimeric amino compounds, one with the stereochemistry exactly as in the natural avermectins with an equatorial (or alpha) substituent and one with the axial (or beta) configuration. The latter is called 4"- or 4'-epi. The reaction gives usually both compounds, and since both possess high biological activities, they may not be separated. Often the 4"-epi compounds are formed to a greater extent. Both epimers are claimed in this patent, either separate or in mixture. As a variation to the foregoing amination reaction, alkyl ammonium salts could be used in place of the ammonium salts to prepare the mono alkyl substituted compounds directly. The same reagents, salts and conditions as described above can be used for such a reaction.

The substitution reaction at the newly formed amino group wherein the substituent is a substituted acyl functionality is carried out using an acylating reagent in the presence of a base in an inert solvent. The preferred acylating reagents are loweralkanoyl anhydrides, loweralkanoyl halides, substituted benzoyl chlorides and the like. The reaction is carried out in an inert solvent such as methylene chloride in the presence of a non-reactive base such as pyridine or triethylamine in order to neutralize the acid produced during the course of the reaction. The reaction temperature is from $-10°$ to 25° C. and the reaction is complete in from 5 minutes to 1 hour. The produce is isolated using known techniques. The aminoderivatives can also be acylated with appropriately substituted acylchlorides, acylanhydrides, mixed acylanhydrides, acylazides, or any form of activated acyl group known to form amide bonds. Since the aminogroup is more reactive towards acylation, any hydroxygroups present at the 5, 7, or 23 positions need not be protected during this conversion. These substituted acylaminoavermectin compounds are isolated using techniques known to those skilled in the art.

Alternatively the 4"- or 4'-substituted acylaminoavermectin compounds can be further modified.

All of the foregoing reactions carried out at the 4"-position of the avermectin can be carried out at the 4'-position of the monosaccharide to afford the correspondingly substituted monosaccharide derivatives.

BIOLOGICAL ACTIVITIES OF THE INSTANT COMPOUNDS

The novel compounds of this invention have significant parasiticidal activity as anthelmintics, ectoparasiticides, insecticides, and acaracides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compounds of this invention have unexpectedly high activity against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites (Tetranychus sp.) aphids (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 5% by weight of the active compound. Preferred drench formulations may contain from 0.001 to 0.1% by weight active compound. The capsules or boluses are comprised of the active ingredient admixed with a carrier vehicle such as starch, talc, magnesium stearate, or di-calcium phosphate.

Where it is desired to administer the avermectin derivatives in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be administered via the animal feedstuff, it is intimately dispersed in the feed or used as a top dressing or in the form of pellets which may then be added to the finished feed or optionally fed separately. Alternatively, the antiparasitic compounds of our invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other parenteral vehicles such as organic preparations using solketal, glycerol formal, and aqueous parenteral formulations are also used. The active avermectin compound or compounds are dissolve or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites, and other biting insects in domesticated animals and poultry. They are also effective in treatment of parasitic diseases that occur in other animals including humans. The optimum amount to be employed for the best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the individual avermectin components may be used, or other active compounds not related to the compounds of this invention.

The compounds of this invention are also useful in combatting agricultural pests that inflict damage upon crops while they are growing or in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the following examples are generally isolated as amorphous solids and not as crystalline solids. They are thus characterized analytically using techniques such as mass spectrometry, nuclear magnetic resonance spectrometry an the like. Being amorphous, the compounds are not characterized by sharp melting points, however, the chromatographic and analytical methods employed indicate that the compounds are pure.

EXAMPLE 1

5-O-tert-Butyldimethylsilyl-4"-deoxy-4"-epi-(N-methoxyacetyl)aminoavermectin B1a/B1b Methoxyacetyl chloride, 0.019 ml, was added to a stirred solution of 4"-epi-amino-5-O-tert-butyldimethylsilyl-4"-deoxyavermectin B1a/B1b, 197 mg, and diisopropylethylamine, 0.16 ml, in 5.0 ml of methylene chloride in an ice bath at $-10°$ to $-20°$ C. After 1.5 hours the reaction was diluted with methylene chloride, washed with aqueous sodium bicarbonate, dried over sodium sulfate and evaporated under reduced pressure to give 220 mg of residue. Purification by column chromatography on silica gel using methylene chloride containing 1% methanol as solvent gave 212 mg of 5-O-tert-butyldimethylsilyl-4"-deoxy-4"-epi-(N-methoxyacetyl)aminoavermectin B1a/B1b, which was characterized by nuclear magnetic resonance and mass [1064 $M+Li)^+$] spectra, and by high pressure liquid chromatographic analyses.

EXAMPLE 2

4"-Deoxy-4"-epi-(N-methoxyacetyl)aminoavermectin B1a/B1b

A solution of 5-O-tert-butyldimethylsilyl-4"-deoxy-4"-epi-(N-methoxyacetyl)aminoavermectin B1a/B1b, 105 mg, in 4.0 ml of anhydrous hydrogen fluoride-pyridine-tetrahydrofuran solution (prepared from 1 part of commercial hydrogen fluoride-pyridine-70:30-solution, 3 parts of pyridine, and 6 parts of tetrahydrofuran) was stirred at room temperature for 3 hours and then left overnight in a freezer. The reaction mixture was poured into a stirred solution of aqueous sodium bicarbonate, and the product was extracted with methylene chloride. The methylene chloride solution was washed with aqueous sodium bicarbonate, dried over sodium sulfate and evaporated under reduced pressure. Chromatography of the residue on a column of silica using methylene chloride containing 1 to 3% of methanol gave 73 mg of 4"-deoxy-4"-epi-(N-methoxyacetyl)aminoavermectin B1a/B1b which was characterized by nuclear magnetic resonance and mass spectra (943, $M^+$), and by high pressure liquid chromatographic analyses.

EXAMPLE 3

4"-Deoxy-4"-epi-(N-methoxyacetyl-N-methyl)aminoavermectin B1a/B1b

Diisopropylcarbodiimide, 0.442 ml, was added to a stirred solution of 4"-deoxy-4"-epi-methoxyacetyl)aminoavermectin B1a/B1b, 1.00 g, and methoxyacetic acid, 0.182 ml, in 15 ml of tetrahydrofuran at room temperature. After 90 minutes and 3.5 hours additional quantities of 0.220 and 0.442 ml of diisopropylcarbodiimide were added. After 5 hours a precipitate was filtered off and rinsed with methylene chloride. Then the filtrate was washed with aqueous sodium bicarbonate, dried over sodium sulfate and evaporated under reduced pressure. The residue was dissolved in benzene and a precipitate which formed upon addition of hexane was filtered off. The filtrate was concentrated under reduced pressure leaving 1.21 g of residue. This was chromatographed on a column of silica gel using methylene chloride containing 1 to 5% of methanol giving 641 mg of 4"-deoxy-4"-epi-(N-methoxyacetyl-N-methyl)aminoavermectin B1a/B1b, which was characterized by nuclear magnetic resonance and mass spectra [1072 $(M+H)^+$], and by high pressure liquid chromatographic analyses.

EXAMPLE 4

4"-Deoxy-4"-epi-(N-methoxyacetyl-N-methyl)amino-5-oxoavermectin B1a/B1b

A solution of 500 mg of 4"-deoxy-4"-epi-(N-methoxyacetyl-N-methyl)aminoavermectin B1a/B1b (obtained as described in Example 3) in 50 ml of ether is stirred with 3.0 g of activated manganese dioxide at room temperature for 18 hours. Then the product is isolated by dilution of the reaction mixture with ethyl acetate and filtration through a sintered glass funnel. The $MnO_2$ is washed repeatedly with methylene chloride. The filtrate is combined and concentrated in vacuo to a light colored glass, which is shown to be more than 90% pure by high performance liquid chromatography and is characterized by its mass and 1H-NMR spectra as 4"-deoxy-4"-epi-(N-methoxyacetyl-N-methyl)amino-5-oxo-avermectin B1a/B1b.

EXAMPLE 5

4"-Deoxy-4"-epi-(N-methoxyacetyl-N-methyl)aminoavermectin B1a/B1b 5-ketoxime

A solution of 380 mg of 4"-deoxy-4"-epi-(N-methoxyacetyl-N-methyl)amino-5-oxoavermectin B1a/B1b, 1.5 ml of dry pyridine, and 300 mg of hydroxylamine hydrochloride in 15 ml of dry ethanol is stirred 2.5 hours at room temperature. Then the ethanol is removed in vacuo at room temperature, and the residue is distributed between water and ethyl acetate. The ethyl acetate extract is washed with water, dried with MgSO$_4$, and concentrated in vacuo to a yellow glass. Purification by silica gel column chromatography with methylene chloride containing from 2.5 to 7.5% of methanol gives the desired product. Further purification by preparative silica gel layer chromatography using a methylene chloride-methanol (9:1) solvent mixture gives pure 4"-deoxy-4"-epi-(N-methoxyacetyl-N-methyl)aminoavermectin B1a/B1b 5-ketoxime as a foam, which is characterized by its mass and 1H-NMR spectra.

EXAMPLE 6

5-O-tert-Butyldimethylsilyl-4"-deoxy-4"-epi-(N-methylthioacetyl)aminoavermectin B1a/B1b Dicyclohexylcarbodiimide, 31 mg, in 0.5 ml of methylene chloride was added to a stirred solution of 4"-epi-amino-5-O-tert-butyldimethylsilyl-4"-deoxyavermectin B1a/B1b, 98.5 mg, and methylthioacetic acid, 0.0104 ml, in 1.5 ml of methylene chloride at room temperature. After 3.0 hours the reaction mixture was filtered, and the filtrate was evaporated under reduced pressure. Chromatography of the residue on a column of silica gel using methylene chloride containing 0.5 to 2% of methanol gave 100 mg of 5-O-tert-butyldimethylsilyl-4"-deoxy-4"-epi-(N-methylthioacetyl)aminoavermectin B1/B1b, which was characterized by nuclear magnetic resonance spectra [2.15 ppm (3H, s, CH3S)] and by high pressure liquid chromatographic analyses.

EXAMPLE 7

4"-Deoxy-4"-epi-(N-methylthioacetyl)aminoavermectin B1a/B1b

A solution of 5-O-tert-butyldimethylsilyl-4"-deoxy-4"-epi-(N-methylthioacetyl)aminoavermectin B1a/B1b, 98 mg, was treated with 2.0 ml of hydrogen fluoride-pyridine-tetrahydrofuran mixture as fully described in Example 2 furnishing 35 mg of 4"-deoxy-4"-epi-(N-methylthioacetyl)aminoavermectin B1a/B1b, which was characterized by nuclear magnetic resonance and mass spectra[966M+Li)+], and by high pressure liquid chromatographic analyses.

EXAMPLE 8

5-O-tert-Butyldimethylsilyl-4"-deoxy-4"-epi-(N-methoxycarbonyl-N-methyl)aminoavermectin B1a/B1b Methyl chloroformate, 0.0085 ml, was added to a stirred solution of 4"-epi-amino-5-O-t-butyldimethylsilyl-4"-deoxyavermectin B1a/B1b, 100 mg, and diisopropylethylamine, 0.080 ml, in 1.5 ml of methylene chloride at room temperature. After 24 hours the reaction was diluted with methylene chloride, washed with aqueous sodium bicarbonate and evaporated under reduced pressure. The residue, 125 mg, was chromatographed on a column of silica gel using methylene chloride containing 1% of methanol to furnish 92 mg of 5-O-tert-butyldimethylsilyl-4"-deoxy-4"-epi-(N-methoxycarbonyl-N-methyl)aminoavermectin B1a/B1b, which was characterized by nuclear magnetic resonance and mass spectra [1058 (M+H)+], and by high pressure liquid chromatographic analyses.

EXAMPLE 9

4"-Deoxy-4"-epi-(N-methoxycarbonyl-N-methyl)aminoavermectin B1a/B1b

5-O-tert-Butyldimethylsilyl-4"-deoxy-4"-epi-(N-methoxycarbonyl-N-methyl)aminoavermectin B1a/B1b, 90 mg, was treated with 1.0 ml of hydrogen fluoride-pyridine-tetrahydrofuran solution for 4.5 hours at room temperature as described in Example 2. Chromatography of the residue using 1 to 5% methanol-methylene chloride gave 70 mg of 4"-deoxy-4"-epi-(N-methoxycarbonyl-N-methyl)aminoavermectin B1a/B1b which was characterized by nuclear magnetic resonance, mass spectra [944 (M+H)+] and high pressure liquid chromatographic analyses.

EXAMPLE 10

5-O-tert-Butyldimethylsilyl-4"-deoxy-4"-epi-(N-methoxy-carbonyl)aminoavermectin B1a/B1b Methyl chloroformate, 0.035 ml, 4"amino-5-O-tert-butyldimethylsilyl-4"-deoxyavermectin B1a/B1b, 400 mg, and diisopropylethylamine, 0.17 ml, were reacted as described in Example 8 furnishing 350 mg of 5-O-tert-butyldimethylsilyl-4"-deoxy-4"-epi-(N-methoxycarbonyl)aminoavermectin B1a/B1b which was characterized by nuclear magnetic resonance, mass spectra [1050 (M+Li)+] and high pressure liquid chromatographic analyses.

EXAMPLE 11

4"-Deoxy-4"-epi-(N-methoxycarbonyl)aminoavermectin B1a/B1b

5-O-tert-Butyldimethylsilyl-4"-deoxy-4"-epi-(N-methoxycarbonyl)aminoavermectin B1a/B1b, 350 mg, was treated with 2.5 ml of hydrogen fluoride-pyridine-tetrahydrofuran solution as fully described in Example 2. Purification by column and thin layer chromatography on silica gel using 1 to 3% methanol-methylene chloride gave 203 mg of 4"-deoxy-4"-epi-(N-methoxycarbonyl)aminoavermectin B1a/B1b which was characterized by nuclear magnetic resonance, mass spectra [936 (M+Li)+] and high pressure liquid chromatographic analyses.

EXAMPLE 12

5-O-t-Butyldimethylsilyl-4"-deoxy-4"-epi-(methylaminocarbonyl)aminoavermectin B1a/B1b A solution of 197 mg of 4"-epi-amino-5-O-t-butyldimethylsilyl-4"-deoxyavermectin B1a/B1b and 0.118 ml of methyl isocyanate in 1.5 ml of methylene chloride was stirred at room temperature. After 24 hours the reaction solution was diluted with methylene chloride, washed with aqueous sodium bicarbonate, dried over anhydrous sodium sulfate and evaporated under reduced pressure furnishing 198 mg of residue. Purification by column chromatography on silica gel using methylene chloride-methanol-water (97:3:0.3) gave 91 mg of product. Further purification by preparative thick layer chromatography on silica gel using methylene chloride-acetone (85:15) provided 78 mg of 5-O-t-butyldimethylsilyl-4"-deoxy-4"-epi-(methylaminocarbonyl)aminoavermectin B1a/B1b, which was characterized by nuclear magnetic resonance and mass spectra

[1049 (M+Li)+], and by liquid high performance chromatography.

EXAMPLE 13

4''-Deoxy-4''-epi-(methylaminocarbonyl)aminoavermectin B1a/B1b

A solution of 75 mg of 5-O-t-butyldimethylsilyl-4''-deoxy-4''-epi-(methylaminocarbonyl)aminoavermectin B1a/B1b in 4.0 ml of 0.5% p-toluenesulfonic acid monohydrate in methanol was stirred at room temperature. After 2 hours it was diluted with methylene chloride, washed with aqueous sodium bicarbonate, dried over sodium sulfate and evaporated under reduced pressure leaving 44 mg of a residue. Purification by silica gel layer chromatography using methylene chloride-acetone (80:20) furnished 20 mg of 4''-deoxy-4''-epi-(methylaminocarbonyl)aminoavermectin B1a/B1b, which was characterized by nuclear magnetic resonance and mass spectra [935 (M+Li)+], and by high pressure liquid chromatographic analyses.

EXAMPLE 14

4''-Deoxy-4''-(dimethylaminomethyleneimino)avermectin B1a/B1b

A solution of 900 mg of 4''-epi-amino-4''-deoxyavermectin B1a/B1b in 20 ml of N,N-dimethylformamide dimethylacetal was left at room temperature for 24 hours. Then the reaction mixture was concentrated in high vacuum to 1.2 g of an orange foam. Attempted purification by silicagel column chromatography with methylene chloride-ethanol-conc. aqueous ammonia in a ratio of 90:10:1 gave 600 mg of a yellow foam. Further purification by preparative silica gel layer chromatography with the same solvent mixture gave 250 mg of 4''-deoxy-4''-(dimethylaminomethyl-eneimino)avermectin B1a/B1b, which was characterized by its mass and NMR spectra. A solution of 200 mg of this and 22 mg of benzoic acid in benzene was lyophilized to afford 4''-deoxy-4''-(dimethylaminomethyleneimino)avermectin B1a/B1b benzoate as a white amorphous powder.

EXAMPLE 15

4''-Deoxy-4''-epi-(N-methoxyacetyl)amino-5-oxoavermectin B1a/B1b

A solution of 100 mg of 4''-deoxy-4''-epi-(N-methoxyacetyl)aminoavermectin B1a/B1b (from example 2) in 3.5 ml of anhydrous dimethylformamide is stirred with 82 mg of pyridinium dichromate at room temperature for 45 minutes. The reaction is worked up with water and ether, and the washed ether phase is concentrated in vacuo to a colorless glass, which is characterized by its mass and NMR spectra as 4''-deoxy-4''-epi-(N-methoxyacetyl)-amino-5-oxoavermectin B1a/B1b.

EXAMPLE 16

4''-Deoxy-4''-epi-(N-methoxyacetyl)acetylaminoavermectin B1a/B1b 5-ketoxime

A solution of 100 mg of crude 4''-deoxy-4''-epi-(methoxyacetyl)amino-5-oxoavermectin B1a/B1b, 75 mg of hydroxylamine hydrochloride, and 0.36 ml of pyridine in 3.6 ml of ethanol is stirred at room temperature for 75 minutes. Then the reaction mixture is concentrated in vacuo to a solid residue. This is worked up with water and ethyl acetate, and the organic phase is dried and concentrated in vacuo to a solid residue. Purification by preparative reverse phase high performance liquid chromatography on a Waters Magnum 20 column using a 75% of a acetonitrile-methanol-3:2 mixture and 25% of water gives pure 4''-deoxy-4''-epi-(N-methoxyacetyl)aminoavermectin B1a/B1b 5-ketoxime, which is characterized by its mass and NMR spectra.

EXAMPLE 17

4''-Deoxy-4''-epi-(N-methylsulfinylacetyl)aminoavermectin B1a/B1b

A solution of 80% m-chloroperbenzoic acid, 50.3 mg, in 0.5 ml of dry methylene chloride is added dropwise to a solution of 4''-deoxy-4''-epi-(N-methylthioacetyl)aminoavermectin B1a/B1b, 224 mg, in 5.0 ml of dry methylene chloride with stirring at 0° C. After 5 minutes aqueous sodium bicarbonate is added. The produce is extracted with methylene chloride. The methylene chloride solution is then extracted with aqueous sodium bicarbonate, dried over sodium sulfate and evaporated under reduced pressure. Chromatography of the residue on a column of silica gel using increasing concentrations of methanol in methylene chloride gives 4''-deoxy-4''-epi-(N-methylsulfinylacetyl)aminoavermectin B1a/B1b.

EXAMPLE 18

4''-Deoxy-4''-epi-(N-methylsulfonylacetyl)aminoavermectin B1a/B1b

A solution of 80% m-chloroperbenzoic acid, 131 mg, in 1.2 ml of dry methylene chloride is added dropwise to a solution of 4''-deoxy-4''-epi-(N-methylthioacetyl)aminoavermectin B1a/B1b, 224 mg, in 5.0 ml of dry methylene chloride with stirring at 0° C. After 1 hour the reaction solution is worked up and purified as described in Example 17 giving 4''-deoxy-4''-epi-(N-methylsulfonylacetyl)aminoavermectin B1a/B1b.

EXAMPLE 19

5-O-tert.-Butyldimethylsilyl-4''-deoxy-4''-epi-(N-methylthioacetyl)aminoavermectin B1a/B1b monosaccharide A solution of 4'-epi-amino-5-O-tert.-butyldimethylsilyl-4''-deoxyavermectin B1a/B1b monosaccharide, 84.1 mg, and methylthioacetic acid, 0.0104 ml, is treated with 31 mg of dicyclohexylcarbodiimide as described in Example 6 furnishing 5-O-tert.-butyldimethylsilyl-4''-deoxy-4''-epi-(N-methylthioacetyl)aminoavermectin B1a/B1b monosaccharide.

EXAMPLE 20

4''-Deoxy-4''-epi-(N-methylthioacetyl)aminoavermectin B1a/B1b monosaccharide

5-O-tert.-Butyldimethylsilyl-4''-deoxy-4''-epi-(N-methylthioacetyl)aminoavermectin B1a/B1b monosaccharide is treated with a solution of hydrogen fluoride-pyridine-tetrahydrofuran by the procedure of Example 2 furnishing 4''-deoxy-4''-epi-(N-methylthioacetyl)aminoavermectin B1a/B1b monosaccharide.

EXAMPLE 21

5-O-tert.-Butyldimethylsilyl-4''-deoxy-4''-epi-N-(2-hydroxypropionyl)aminoavermectin B1a/B1b 4''-epi-Amino-O-tert.-butyldimethylsilyl-4''-deoxyavermectin B1a/B1b, 296 mg, in 6.0 ml of methyl lactate was stirred at 85° C. under $N_2$. After 14 days the reaction solution was diluted with methylene chloride, extracted with aqueous sodium bicarbonate, dried over sodium sulfate and evaporated under reduced pressure. The residue was purified on a column of silica gel using methylene chloride-acetone (90:10) furnishing 119 mg of 5-O-tert.-butyldimethylsilyl-4"-deoxy-4"-epi-N-(2-hydroxypropionyl)aminoavermectin B1a/B1b which was characterized by nuclear magnetic resonance, mass spectra [1063 (M+Li)+] and high pressure liquid chromatographic analyses.

EXAMPLE 22

4"-Deoxy-4"-epi-N-(2-hydroxypropionyl)aminoavermectin B1a/B1b

A solution of 5-O-tert.-butyldimethylsilyl-4"-deoxy-4"-epi-N-(2-hydroxypropionyl)aminoavermectin B1a/B1b, 88 mg, in 1.6 ml of methanolic 1.0% p-toluenesulfonic acid monohydrate was stirred at −12° C. for 30 minutes and then set in the freezer at −16° C. After 21 hours the reaction solution was worked up and purified as described in Example 13 furnishing 33 mg of 4"-deoxy-4"-epi-N-(2-hydroxypropionyl)amino avermectin B1a/B1b which was characterized by nuclear magnetic resonance, mass spectra [944 (M+H)+] and high pressure liquid chromatographic analyses.

EXAMPLE 23

5-O-tert.-Butyldimethylsilyl-4"-epi-N-(4-chlorobenzoyl)amino-4"-deoxyavermectin B1a/B1b A solution of 4-chlorobenzoyl chloride, 38.5 mg, in 1.1 ml methylene chloride was added to a stirred solution of 4"-epi-amino-5-O-tert.-butyldimethylsilyl-4"-deoxyavermectin B1a/B1b, 197 mg, and diisopropylethylamine, 0.086 ml, in 3.0 ml of methylene chloride at room temperature, 23° C. After 3 hours the reaction solution was worked up and the residue purified as described in Example 1 furnishing 159 mg of 5-O-tert.-butyldimethylsilyl-4"-epi-N-(4-chlorobenzoyl)amino-4"-deoxyavermectin B1a/B1b which was characterized by nuclear magnetic resonance, mass spectra [1130 (M+Li)+] and high pressure liquid chromatographic analyses.

EXAMPLE 24

4"-epi-N-(4-Chlorobenzoyl)amino-4"-deoxyavermectin B1a/B1b

A solution of 5-O-tert.-butyldimethylsilyl-4"-epi-[N-(4-chlorobenzoyl)amino]-4"-deoxyavermectin B1a/B1b, 142 mg, was treated with hydrogen fluoride-pyridine-tetrahydrofuran, 2.5 ml, by the procedure of Example 2 furnishing 117 mg of 4"-epi-N-(4-chlorobenzoyl)amino-4"-deoxyavermectin B1a/B1b which was characterized by nuclear magnetic resonance, mass spectra [1016 (M+Li)+] and high pressure liquid chromatographic analyses.

EXAMPLE 25

5-O-tert.-Butyldimethylsilyl-4"-deoxy-4"-epi-(N-nicotinoyl)aminoavermectin B1a/B1b Nicotinoyl chloride, 34 mg, was added to a stirred solution of 4"-epi-amino-5-O-tert.-butyldimethylsilyl-4"-deoxyavermectin B1a/B1b and diisopropylethylamine, 0.180 ml, in 4.0 ml of dry methylene chloride at room temperature, 23° C. Reaction was incomplete after 2 days. Another 34 mg of nicotinoyl chloride was added. After another 5 days, the reaction solution was worked up and the residue purified as described in Example 1 using ethyl acetate for column elution. 142 Mg of 5-O-tert.-butyldimethylsilyl-4"-deoxy-4"-epi-(N-nicotinoyl)aminoavermectin B1a/B1b was obtained and characterized by nuclear magnetic resonance, mass spectra [1091 (M+H)+] and high pressure liquid chromatographic analyses.

EXAMPLE 26

4"-Deoxy-4"-epi-(N-nicotinoyl)aminoavermectin B1a/B1b

A solution of 5-O-tert.-butyldimethylsilyl-4"-deoxy-4"-epi-(N-nicotinoyl)aminoavermectin B1a/B1b, 130 mg, was treated with 3.0 ml of hydrogen fluoride-pyridine-tetrahydrofuran by the procedure of Example 2. 90 Mg of 4"-deoxy-4"-epi-(N-nicotinoyl)aminoavermectin B1a/B1b was obtained and characterized by nuclear magnetic resonance, mass spectra [977 (M+H)+] and high pressure liquid chromatographic analyses.

EXAMPLE 27

5-O-tert.-Butyldimethylsilyl-4"-epi-(N-cyclohexanecarbonyl)amino-4"-deoxyavermectin B1a/B1b Cyclohexanecarbonyl chloride, 0.028 ml, was added to a stirred solution of 4"-epi-amino-5-O-tert.-butyldimethylsilyl-4"-deoxyavermectin B1a/B1b, 197 mg, and diisopropylethylamine, 0.086 ml, in 3.5 ml of dry methylene chloride at room temperature. After 6 hours the reaction solution was worked up and the product purified as described in Example 1 furnishing 193 mg of 5-O-tert.-butyldimethylsilyl-4"-epi-(N-cyclohexanecarbonyl)amino-4"-deoxyavermectin B1a/B1b which was characterized by nuclear magnetic resonance, mass spectra [1102 (M+Li)+] and high pressure liquid chromatographic analyses.

EXAMPLE 28

4"-epi-(N-Cyclohexanecarbonyl)amino-4"-deoxyavermectin B1a/B1b

A solution of 5-O-tert.-butyldimethylsilyl-4"-deoxy-4"-epi-(N-cyclohexanecarbonyl)aminoavermectin B1a/B1b, 190 mg, was treated with 3.0 ml of hydrogen fluoride-pyridine-tetrahydrofuran at room temperature, 23° C., for 16 hours by the procedure of Example 2. 128 Mg of 4"-deoxy-4"-epi-(N-cyclo-hexanecarbonyl)aminoavermectin B1a/B1b was obtained and characterized by nuclear magnetic resonance, mass spectra [982 (M+H)+] and high pressure liquid chromatographic analyses.

EXAMPLE 29

5-O-tert-Butyldimethylsilyl-4"-epi-(N-chloroacetyl)amino-4"-deoxyavermectin B1a/B1b Chloroacetyl chloride, 0.017 ml, was added to a stirred solution of 4"-epi-amino-5-O-tert.-butyldimethylsilyl-4"-deoxyavermectin B1a/B1b, 197 mg, and diisopropylethylamine, 0.120 ml, in 2.0 ml of dry methylene chloride at room temperature. After 20 hours the reaction solution was worked up and the product purified as described in Example 1 furnishing 184 mg of 5-O-tert.-butyldimethylsilyl-4"-epi-(N-chloroacetyl)amino-4"-deoxyavermectin B1a/B1b which was characterized by nuclear magnetic resonance, mass spectra [1068 (M+Li)+] and high pressure liquid chromatographic analyses.

EXAMPLE 30

4"-epi-(N-chloroacetyl)amino-4"-deoxyavermectin B1a/B1b

A solution of 5-O-tert.-butyldimethylsilyl-4"-deoxy-4"-epi-(N-chloroacetyl)aminoavermectin B1a/B1b, 160 mg, was treated with 1.3 ml of hydrogen fluoride-pyridine-tetrahydrofuran mixture for 17 hrs at room temperature, 23° C. by the procedure of Example 2. 128 Mg of 4"-deoxy-4"-epi-(N-chloroacetyl)aminoavermectin B1a/B1b was obtained and characterized by nuclear magnetic resonance, mass spectra [947 (M+H)+] and high pressure liquid chromatographic analyses.

EXAMPLE 31

5-O-Diethoxymethyl-4"-deoxy-4"-epi-[N-(morpholin-4-yl)methylidene]aminoavermectin B1a/B1b A solution of 4"-epi-amino-4"-deoxyavermectin B1a/B1b, 600 mg, in 9.0 ml of triethyl orthoformate was heated at 130° C. for 35 minutes while distilling off the liberated ethanol. The reaction solution was evaporated to dryness in high vacuum. The residue was dissolved in 8.0 ml of toluene and 0.600 ml of morpholine. The solution was heated at 80° C. for 60 minutes and then evaporated under reduced pressure. The residue was purified on a column of neutral alumina using methylene chloride-methanol-conc. ammonia (99.4:0.6:0.06) furnishing 158 mg of 5-O-diethoxymethyl-4"-deoxy-4"-epi-[N-(morpholin-4-yl)methylidene]aminoavermectin B1a/B1b which was characterized by nuclear magnetic resonance, mass spectra [1071 (M+H)+] and high pressure liquid chromatographic analyses.

EXAMPLE 32

4"-Deoxy-4"-epi-[N-(morpholin-4-yl)methylidene]aminoavermectin B1a/B1b

A solution of 5-O-diethoxymethyl-4"-deoxy-4"-epi-[N-(morpholin-4-yl)methylidene]aminoavermectin B1a/B1b, 150 mg, in 7.0 ml of 1.0N aqueous acetic acid and 7.0 ml of methanol was stirred at room temperature, 23° C. After 4.5 hours the solution was made basic by addition of 1.0N aqueous ammonia and then extracted with methylene chloride. The methylene chloride solution was dried over sodium sulfate and evaporated under reduced pressure furnishing 106 mg of 4"-deoxy-4"-epi-[N-(morpholin-4-yl)methylidene]aminoavermectin B1a/B1b which was characterized by nuclear magnetic resonance, mass spectra [969 (M+H)+] and high pressure liquid chromatographic analyses.

EXAMPLE 33

5-O-tert-Butyldimethylsilyl-4"-epi-(N-acetylaminoacetyl)amino-4"-deoxyavermectin B1a/B1b A mixture of 351 mg of N-acetylglycine, 346 mg of N-hydroxysuccinimide 620 mg of dicyclohexylcarbodiimide in dioxane was stirred at room temperature overnight, then filtered, and the filtrate concentrated in vacuo to a gum of the activated ester. 75 mg of this product dissolved in 1 ml of dioxane was added to a solution of 5-O-tert-butyldimethylsilyl-4"-epi-amino-4"-deoxyavermectin B1a/B1b in 5 ml of methylene chloride and stirred over night at room temperature. Then the reaction mixture was washed with water, 1-molar aqueous HCl, water and aqueous NaHCO3 solution, dried over MgSO4 and concentrated in vacuo to 250 mg of residue. Purification by silicagel column chromatography gave 109 mg of 5-O-tert-butyldimethylsilyl-4"-epi-(N-acetylaminoacetyl)amino-4"-deoxyavermectin B1a/B1b, which was characterized by its NMR spectrum.

EXAMPLE 34

4"-Epi-(N-acetylaminoacetyl)amino-4"-deoxyavermectin B1a/B1b

A solution containing 109 mg of 5-O-tert-butyldimethylsilyl-4"-epi-(N-acetylaminoacetyl)amino-4"-deoxyavermectin B1a/B1b in 2 ml of hydrogen fluoride-pyridine-tetrahydrofuran mixture according to the procedure fully described in Example 2 was left 18 hours at room temperature. The crude product was purified by silica gel column chromatography (ethyl acetate with 3% methanol) to give 60 mg of 4"-epi-(N-acetylaminoacetyl)amino-4"-deoxyavermectin B1a/B1b, which was characterized by its UV, mass and NMR spectra, and microanalysis.

EXAMPLE 35

5-O-tert-Butyldimethylsilyl-4"-deoxy-4"-epi-(N-succinimidyl)avermectin B1a/B1b A solution of 100 mg of 5-O-tert-butyldimethylsilyl-4"-epi-amino-4"deoxyavermectin B1a/B1b, 50 mg of 4-dimethylaminopyridine, 50 mg of diisopropylethylamine in 2.5 ml of anhydrous methylene chloride is stirred in an ice bath, when a solution of 45 mg of succinyl chloride in 0.5 ml of methylene chloride is added slowly. The reaction mixture is held for 1 hours at 0° C., then 16 hours at room temperature. Finally it is heated for 30 minutes, then evaporated to dryness in vacuo/high vacuum to an oil. Purification by preparative silica gel layer chromatography gives 5-O-tert-butyldimethylsilyl-4"-deoxy-4"-epi-(N-succinimidyl)avermectin B1a/B1b, which is characterized by its mass and NMR spectra.

EXAMPLE 36

4"-Deoxy-4"-epi-(N-succinimidyl)avermectin B1a/B1b

A solution of 45 mg of 5-O-tert-butyldimethylsilyl-4"-deoxy-4"-epi-(N-succinimidyl)avermectin B1a/B1b in 4.0 ml of methanol containing 40 mg of p-toluenesulfonic acid hydrate is stirred at 18° C. for 30 minutes. Then ethyl acetate is added, the solution washed with dilute NaHCO3 and water, dried and concentrated in vacuo and high vacuum to a foam. Purification by preparative silica gel layer chromatography gives 4"-deoxy-4"-epi-(N-succinimidyl) avermectin B1a/B1b, which is characterized by its mass and NMR spectra.

PREPARATION A

5-O-t-Butyldimethylsilylavermectin B1a/B1b

A solution of 50 g of avermectin B1a/B1b (dried over P2O5 in high vacuum to constant weight), 24 g of imidazole and 24 g of tert-butyldimethylsilyl chloride in 400 ml of anhydrous dimethylformamide was stirred at room temperature for 50 minutes. The reaction mixture was poured into 1.5 l of ice cold water and the aqueous phase was extracted four times with 200 ml of ether. The organic phase was washed twice with water, aqueous sodium chloride solution, dried with magnesium sulfate and concentrated in vacuo to a white foam. The crude product was purified by silica gel column chromatography with a methylene chloride-ethyl acetate- 90:10 to 70:30 solvent system to give 46.5 g of 5-O-t-butyldimethylsilylavermectin B1a/B1b as an amorphous foam, which was characterized by its 1H-NMR- and mass spectra.

PREPARATION B

5-O-t-Butyldimethylsilyl-4"-oxoavermectin B1a/B1b

To a solution containing 9.1 ml of oxalyl chloride in 230 ml of dry methylene chloride stirred at −60° C. was added 15 ml of dry dimethylsulfoxide 15 min. Then a solution of 46.5 g of 5-O-t-butyldimethylsilyl avermectin B1a/B1b dissolved in 230 ml of dry methylene chloride was added over a period of 15 minutes while maintaining the temperature at −60° C. The reaction mixture was stirred at this temperature for 30 minutes when 65 ml of dry triethylamine was added. The mixture was stirred for 5 additional minutes at −60° C., and then the cooling bath was removed and the reaction mixture was allowed to come to ambient temperature. After addition of water the reaction product was extracted with methylene chloride, the extract was washed with water, dried and concentrated in vacuo to 45.5 g of a yellow foam. This was identified by its mass and NMR spectra as 5-O-t-butyldimethylsilyl-4"-oxoavermectin B1a/B1b, which was used for further chemical reactions without purification.

PREPARATION C

5-O-t-Butyldimethylsilyl-4"-deoxy-4"-epi-methylamino-avermectin B1a/B1b

A solution of 26 ml of glacial acetic acid in 300 ml of MeOH was treated with methylamine gas at 0° C. until the pH of the solution reached 9.0. To this a solution containing 44.5 g of 5-O-t-butyldimethylsilyl-4"-oxoavermectin B1a/B1b in 200 ml of methanol was added, and the reaction mixture was stirred at room temperature for 1 hour, when a solution of 3.5 g of sodium cyanoborohydride in 75 ml of MeOH was added dropwise over 10 min. After 50 min the reaction mixture was poured into 1.5 l of cold aqueous $Na_2CO_3$ solution and the product was extracted with ether. The extract was washed with water, dried, and concentrated in vacuo to 44.8 g of yellow foam. Thin layer chromatography (silica gel, methylene chloride-ethyl acetate 85:15) of the crude product at this point showed several spots. Further purification by silica gel column chromatography using methylene chloride-ethyl acetate solvent mixtures gave 4.7 g of 4"-epi-5-O-t-butyldimethylsilylavermectin B1a/B1b, 1.2 g of 5-O-t-butyldimethylsilyl-4"-deoxy-4"-methylaminoavermectin B1a/B1b, and 14 g of 5-O-t-butyldi-methylsilyl-4"-deoxy-4"-epi-methylaminoavermectin B1a/B1b as light foams, which were characterized by their mass spectrum and their 1H-, and 13C-NMR spectra.

PREPARATION D

4"-Deoxy-4"-epi-methylaminoavermectin B1a/B1b

A solution of 14 g of 5-O-t-butyldimethylsilyl-4"-deoxy-4"-epi-methylaminoavermectin B1a/B1b in 200 ml of methanol and a solution of 7 g of p-toluenesulfonic acid monohydrate in 500 ml of methanol was mixed and stirred at room temperature for 45 minutes, and then poured into dilute aqueous $Na_2CO_3$ solution. The product was extracted with ethyl acetate, washed with water and dried over $MgSO_4$, concentrated in vacuo, and purified by preparative silicagel column chromatography with a methylene chloride-methanol 95:5 solvent mixture to give 6.7 g of 4"-deoxy-4"-epi-methylaminoavermectin B1a/B1b, which was identified by NMR and mass spectra.

PREPARATION E

4"-epi-Amino-5-O-t-butyldimethylsilyl-4"-deoxy-avermectin B1a/B1b

For the reductive amination 12 mg of sodium cyanoborohydride was added to a solution of 200 mg of 5-O-t-butyldimethylsilyl-4"-oxoavermectin B1a/B1b (from preparation B) and 160 mg of ammonium acetate in 3 ml of methanol, and the reaction mixture was stirred at room temperature for 1 hour. Then it was poured into aqueous $Na_2CO_3$ solution, and the organic products were extracted with ethyl acetate. The extract was washed with water, dried, and concentrated in vacuo to 210 mg of yellow oil. Preparative silica gel layer chromatography with 98:2 methylene chloride-methanol solvent gave 26 mg of 4"-amino-5-O-t-butyldimethylsilyl-4"-deoxyavermectin B1a/B1b, and 100 mg of 4"-epi-amino-5-O-t-butyldimethylsilyl-4"-deoxyavermectin B1a/B1b as light foams, which were characterized by their mass and their 1H-, and 13C-NMR spectra.

PREPARATION F

4"-epi-Amino-4"-deoxyavermectin B1a/B1b

A solution of 100 mg of 4"-epi-amino-5-O-t-butyldimethylsilyl-4"-deoxyavermectin B1a/B1b (from preparation E) in 10 ml of methanol containing 1% of p-toluenesulfonic acid monohydrate was kept at room temperature for 30 minutes and then poured into aqueous $NaHCO_3$ solution. The product was isolated by extraction with ethyl acetate, and obtained in pure form after preparative silica gel layer chromatography as 55 mg of a light yellow foam, which was characterized by its mass and NMR spectra as 4"-epi-amino-4"-deoxyavermectin B1a/B1b.

PREPARATION G 22,23-Dihydro-4"-oxo-5-O-tert-butyldimethylsilyl-avermectin B1a/B1b To a solution of 97 μl of oxalyl chloride in 2.5 ml of methylene chloride stirred at −60° C. a solution of 160 μl of dimethylsulfoxide in 1.0 ml of methylene chloride was added dropwise over 3 minutes from a syringe. Then a solution of 500 mg of 22,23-dihydro-5-O-tert-butyldimethylsilyl-avermectin B1a/B1b in 3.0 ml of methylene chloride was added by syringe dropwise during 5 minutes. The reaction mixture was stirred at −60° C. for 30 minutes, when 0.71 ml of triethylamine was added dropwise. After another 5 minutes at −60° C. the cooling bath was removed, and the reaction mixture was allowed to come to room temperature. Addition to water, extraction with ether, washing with water, drying and concentration in vacuo gave 520 mg of a yellow foam, which was purified by preparative silica gel layer chromatography with a methylene chloride-ethyl acetate-9:1 solvent mixture to give 470 mg of pure 22,23-dihydro-4"-oxo-5-O-tert-butyldimethylsilyl-avermectin B1a/B1b, which was characterized by its mass and 300 mHz 1H-NMR spectra.

PREPARATION H

4"-Oxoavermectin B1a/B1b

A cold (0° to 5° C.) solution of 5-O-tert-butyldimethylsilyl-4"-oxoavermectin B1a/B1b (obtained through .preparation B), 5.50 gm (5.40 mMole), and methanolic 1.0% p-toluenesulfonic acid monohydrate, 120 mL (6.2 mMole), was stirred for 50 minutes and then poured into aqueous sodium bicarbonate. The product was extracted with methylene chloride. The methylene chloride solutions were combined, dried over anhydrous sodium sulfate and evaporated under reduced pressure providing 4.5 gm of 4"-oxoavermectin B1a/B1b which was characterized by nuclear magnetic resonance, mass spectra [871 (M+H)+] and high pressure liquid chromatographic analyses.

PREPARATION I

Avermectin B1a/B1b monosaccharide

Avermectin B1a/B1b, 6.0 g, was dissolved in a stirred solution of iso-propanol containing 1.5 ml of conc. sulfuric acid at room temperature, 23° C. After 41 hours the solution was concentrated under reduced pressure to 75 ml and then diluted with 25 ml of water and 75 ml of ethyl acetate. The mixture was neutralized with 50% aqueous sodium hydroxide and the layers were separated. The aqueous solution was extracted with ethyl acetate. The ethyl acetate solutions were combined, extracted with water, dried over sodium sulfate and evaporated under reduced pressure. Flash chromatography of the residue using silica gel and hexane-acetone (3:1) furnished 3.1 g of avermectin B1a/B1b monosaccharide which was characterized by nuclear magnetic resonance, mass spectra [735 (M+Li)+] and high pressure liquid chromatographic analyses.

PREPARATION J

5-O-tert-Butyldimethylsilyl-avermectin B1a/B1b monosaccharide

Avermectin B1a/B1b monosaccharide, 2.51 g, is treated with 1.44 g of imidazole and 1.44 g of tert.-butyldimethylsilyl chloride in 25 ml of anhydrous dimethylformamide by the procedure of Preparation A furnishing 5-O-tert-butyldimethylsilyl-avermectin B1a/B1b monosaccharide.

PREPARATION K

5-O-tert-Butyldimethylsilyl-4'-oxoavermectin B1a/B1b monosaccharide

5-O-tert-Butyldimethylsilyl-avermectin B1a/B1b monosaccharide, 2.1 g, is treated with of 0.49 ml of oxalyl chloride and 0.81 ml of dimethylsulfoxide in methylene chloride solution at $-60°$ C. by the procedure of Preparation B furnishing 5-O-tert-butyldimethylsilyl-4'-oxoavermectin B1a/B1b monosaccharide.

PREPARATION L

4'-epi-Amino-5-O-tert-butyldimethylsilyl-4"deoxyavermectin B1a/B1b monosaccharide 5-O-tert-Butyldimethylsilyl-4'-oxoavermectin B1a/B1b monosaccharide, 840 mg, is treated with 800 mg of ammonium acetate and 60 mg of sodium cyanoborohydride in 15 ml of methanol by the procedure of Preparation E. furnishing 4'-epi-amino-5-O-tert-butyldimethylsilyl-4"-deoxyavermectin B1a/B1b monosaccharide.

What is claimed is:

1. A compound having the formula:

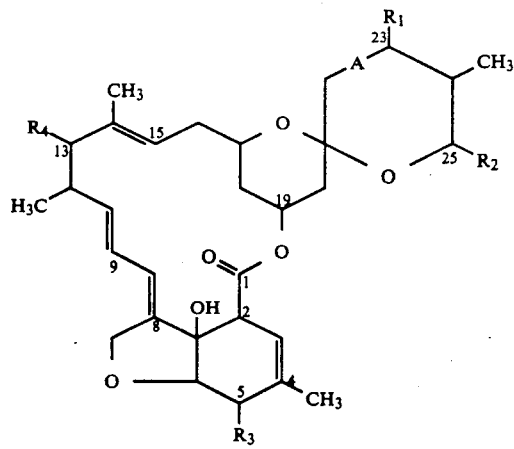

wherein A at the 22,23 position represents a single bond and wherein $R_1$ is hydrogen or hydroxy or oxo, or A represents a double bond and $R_1$ is absent;

$R_2$ is methyl, ethyl, an alpha-branched $C_3-C_8$ alkyl, alkenyl, alkynyl, alkoxyalkyl or alkylthioalkyl group; a $C_3-C_8$ cycloalkyl or $C_5-C_8$ cycloalkenyl group, either of which may optionally be substituted by methylene or one or more $C_1-C_4$ alkyl groups or halo atoms; or a 3 to 6 membered oxygen or sulfur containing heterocyclic ring which may be saturated, or fully or partly unsaturated and which may optionally be substituted by one or more $C_1-C_4$ alkyl groups or halo atoms;

$R_3$ is hydroxy, loweralkoxy, loweralkanoyloxy, oxo or oxime;

$R_4$ is

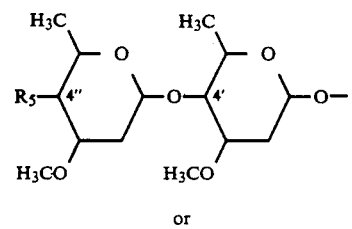

or

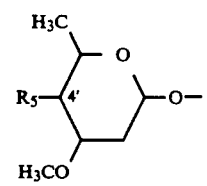

where $R_5$ is $NR_6R_7$, $R_6$ is substituted loweralkanoyl, wherein the substituent is halogen, hydroxy, loweralkoxy, phenoxy, loweralkylthio, loweralkylsulfinyl, loweralkylsulfonyl, amino, loweralkanoylamino, loweralkylamino, haloloweralkoxycarbonylamino, oxo, carboxy or lower alkoxycarbonyl; or $R_6$ is cycloloweralkanoyl, or benzoyl, or substituted benzoyl, wherein the substituent is halogen, loweralkoxy, sulfonamido, amino, loweralkylamino, diloweralkylamino or loweralkanoylamino; or $R_6$ is nicotinoyl;

$R_7$ is hydrogen, loweralkyl, substituted loweralkyl where the substituent is phenyl, hydroxy, loweralkoxy, amino, loweralkylamino, loweralkanoylamino, methylthio, methylsulfonyl or methylsulfinyl;

or $R_5 =$

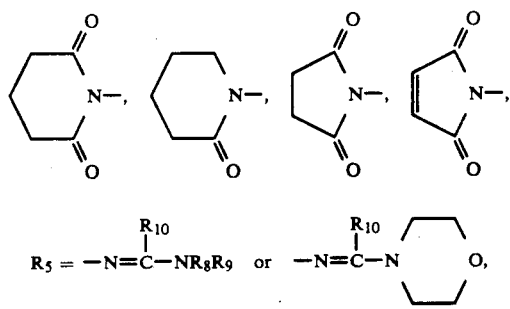

$R_5 = -N=\overset{R_{10}}{\underset{|}{C}}-NR_8R_9$ or $-N=\overset{R_{10}}{\underset{|}{C}}-N\diagup\diagdown O$, $R_5 = -NH-CO-NR_8R_9$, $R_8$, $R_9$ and $R_{10}$ are independently hydrogen or loweralkyl;

or $R_5 = -NH-CN$.

2. A compound of claim 1, wherein A at the 22,23 position represents a single bond and wherein $R_1$ is hydrogen or hydroxy, or A represents a double bond and $R_1$ is absent;

$R_2$ iso-propyl, sec-butyl, or an alpha-branched $C_3$-$C_8$ alkenyl group; and $R_3$ is hydroxy or oxime;

$R_4$ is

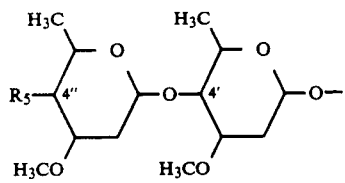

where $R_5$ is $NR_6R_7$, $R_6$ is substituted loweralkanoyl, where the substituent is halogen, hydroxy, loweralkoxy, phenoxy, loweralkylthio, loweralkylsulfinyl, loweralkylsulfonyl, amino, loweralkanoylamino, loweralkylamino, haloloweralkoxycarbonylamino, oxo, carboxy or loweralkoxycarbonyl; or $R_6$ is cycloloweralkanoyl, or benzoyl, or substituted benzoyl, wherein the substituent is halogen, loweralkoxy, sulfonamido, amino, loweralkylamino, diloweralkylamino or loweralkanoylamino; or $R_6$ is nicotinoyl;

$R_7$ is hydrogen, loweralkyl, substituted loweralkyl where the substituent is phenyl, hydroxy, loweralkoxy, amino, loweralkylamino, loweralkanoylamino, methylthio, methylsulfonyl or methylsulfinyl;

or $R_5 = -NH-CO-NR_8R_9$, where $R_8$ and $R_9$ and $R_{10}$ are independently hydrogen or loweralkyl.

3. A compound of claim 1,
wherein A at the 22,23 position represents a single bond and wherein $R_1$ is hydrogen or hydroxy, or A represents a double bond and $R_1$ is absent;

$R_2$ is 2-propyl, 2-butyl, 2-buten-2-yl, 2-penten-2-yl, or 4-methyl-2-penten-2-yl;

$R_3$ is hydroxy;

$R_4$ is

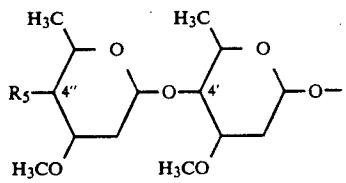

where $R_5$ is $NR_6R_7$, $R_6$ is substituted loweralkanoyl, where the substituent is halogen, hydroxy, loweralkoxy, phenoxy, loweralkylthio, loweralkylsulfinyl, loweralkylsulfonyl, amino, loweralkanoylamino, loweralkylamino, haloloweralkoxycarbonylamino, oxo, carboxy or loweralkoxycarbonyl; or $R_6$ is cycloloweralkanoyl, or benzoyl, or substituted benzoyl, wherein the substituent is halogen, loweralkoxy, sulfonamido, amino, loweralkylamino, diloweralkylamino or loweralkanoylamino; or $R_6$ is nicotinoyl;

$R_7$ is hydrogen, loweralkyl, substituted loweralkyl where the substituent is phenyl;

or $R_5 = -NH-CO-NR_8R_9$, where $R_8$ and $R_9$ and $R_{10}$ are independently hydrogen or loweralkyl.

4. The compound of claim 1, which is 4''-deoxy-4''-epi-methoxyacetylaminoavermectin B1a/B1b.

5. The compound of claim 1, which is 4''-deoxy-22,23-dihydro-4''-epi-(N-methoxyacetyl-N-methylamino)avermectin B1a/B1b.

6. The compound of claim 1, which is 4''-deoxy-4''-epi-methylthioacetylaminoavermectin B1a/B1b.

7. The compound of claim 1, which is 4''-epi-(N-acetylglycylamino)-4''-deoxyavermectin B1a/B1b.

8. The compound of claim 1, which is 4''-deoxy-4''-epi-phenoxyacetylaminoavermectin B2a/B2b.

9. The compound of claim 1, which is 4''-deoxy-4''-epi-nicotinoylamino-4''-avermectin B1a/B1b.

10. The compound of claim 1, which is 4''-deoxy-4''-epi-methoxycarbonylaminoavermectin B1a/B1b.

11. The compound of claim 1, which is 4''-deoxy-4''-epi-methylthioacetylaminoavermectin B1a/B1b monosaccharide.

12. A method for the treatment of parasitic infections of animals, which comprises treating the infected animal with an effective amount of a compound of claim 1.

13. A method for the treatment of parasitic infections of plants, which comprises treating the infected plant, or the soil in which the infected plant grows, with an effective amount of a compound of claim 1.

14. A composition useful for the treatment of animals or plants infected with parasites, which comprises an inert carrier and an effective amount of a compound of claim 1.

* * * * *